United States Patent
Zhou et al.

(10) Patent No.: US 8,557,987 B2
(45) Date of Patent: Oct. 15, 2013

(54) BENZODITHIOPHENE ORGANIC SEMICONDUCTIVE MATERIAL AND ITS PREPARATION METHOD AND USE

(75) Inventors: Mingjie Zhou, Guangdong (CN); Jie Huang, Guangdong (CN); Erjian Xu, Guangdong (CN)

(73) Assignee: Ocean's King Lighting Science & Technology Co., Ltd., Guangdong (CN)

( * ) Notice: Subject to any disclaimer, the term of this patent is extended or adjusted under 35 U.S.C. 154(b) by 0 days.

(21) Appl. No.: 13/821,629

(22) PCT Filed: Sep. 10, 2010

(86) PCT No.: PCT/CN2010/076808
§ 371 (c)(1),
(2), (4) Date: Mar. 8, 2013

(87) PCT Pub. No.: WO2012/031404
PCT Pub. Date: Mar. 15, 2012

(65) Prior Publication Data
US 2013/0165655 A1   Jun. 27, 2013

(51) Int. Cl.
*C07D 241/40*  (2006.01)
(52) U.S. Cl.
USPC ........................................................ 544/353
(58) Field of Classification Search
USPC ........................................................ 544/353
See application file for complete search history.

(56) References Cited

FOREIGN PATENT DOCUMENTS

WO    WO 2010/084865 A1 * 7/2010

* cited by examiner

*Primary Examiner* — Kristin Vajda
(74) *Attorney, Agent, or Firm* — Rosenberg, Klein & Lee (57) ABSTRACT

The present invention relates to optoelectronic materials field, and it discloses a benzodithiophene organic semiconductive material with the following structural formula (P):

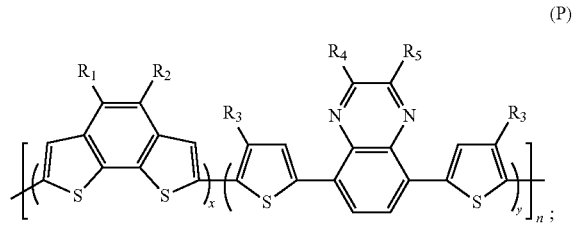

wherein, $x+y=2$; $1 \leq x < 2$, $0 < y \leq 1$; $1 < n \leq 100$; $R_1$, $R_2$ are $C_1$-$C_{20}$alkyl; $R_3$ is selected from $C_1$-$C_{20}$alkyl; $R_4$, $R_5$ are hydrogen, phenyl, $C_1$-$C_{20}$ alkyl or phenyl substituted by $C_1$-$C_{20}$ alkoxy. The present invention is also provided with preparation method and use of the benzodithiophene organic semiconductive material. The benzodithiophene containing bisphenyl siloles unit has good dissolution property, high carrier mobility, strong absorbance, wide optical absorption range, and improved utilization of sunlight, and its preparation process is simple, with high yield, and easy to operate and control.

10 Claims, 2 Drawing Sheets

BENZODITHIOPHENE ORGANIC SEMICONDUCTIVE MATERIAL AND ITS PREPARATION METHOD AND USE

FIELD OF THE INVENTION

The present invention relates to an organic semiconductive material, and more particularly to a benzodithiophene organic semiconductive material.

The present invention also relates to preparation method and use of the benzodithiophene organic semiconductive material.

BACKGROUND OF THE INVENTION

It is always a hot and difficult point in the research field of photovoltaic technology to make solar cells of low cost and high efficiency with cheap materials. At present, silicon solar cells for using on ground is limited to use due to its complexity production process and high cost. In order to reduce cost, and expand the range of uses, for a long time people have been looking for a new type of solar cell material. Polymer solar cells receives much attention due to advantages of low cost of raw materials, light weight, flexibility, simple production process, available preparation in a large area by way of coating, printing, etc., and if energy conversion efficiency could be improved to a level of commercial silicon solar cell, its market prospects will be very huge. Since 1992, N. S. Sariciftci etc. reported photoinduced electron transfer phenomenon between conjugated polymers and C60 in SCIENCE (N. S Sariciftci, L. Smilowitz, A. J. Heeger, et al. Science, 1992, 258, 1474), people have invested a great deal of research in polymer solar cells and achieved rapid development. At present, the research of polymer solar cells is mainly focused on donor/acceptor blend, and the energy conversion efficiency of the polymer solar cells which adopt blend of PTB7 with PC71BM has reached 7.4% (Y. Liang et al, Adv. Mater.; DOI:10.1002/adma.200903528), but it is still lower than that of the inorganic solar cells. Major factors that constraints its performance are: the organic semiconductor device is relatively low carrier mobility, and spectral response of the device dose not match with the solar radiation spectrum, and red area with high photon flux is not be utilized effectively and electrode collection efficiency of carrier is low. In order to make the polymer solar cells be used in practical application, to develop new materials and to significantly improve the energy conversion efficiency are still the primary tasks of this research field.

SUMMARY OF THE INVENTION

An object of the present invention is to provide a benzodithiophene organic semiconductive material to solve the above mentioned problems.

An object of the present invention is to provide a preparation method and use of the benzodithiophene organic semiconductive material.

The benzodithiophene organic semiconductive material according to the present invention has the following structure (P):

wherein, $x+y=2$; $1 \leq x < 2$, $0 < y \leq 1$; $1 < n \leq 100$; $R_1$, $R_2$ are $C_1$-$C_{20}$ alkyl; $R_3$ is selected from $C_1$-$C_{20}$ alkyl; $R_4$, $R_5$ are hydrogen, phenyl, $C_1$-$C_{20}$ alkyl or phenyl substituted by $C_1$-$C_{20}$ alkoxy.

The method for preparing the benzodithiophene organic semiconductive material designed by the present invention is as follows:

In oxygen-free environment, 2,7-bis(trimethyltin)-benzo[2,1-b:3,4-b']dithiophene with a structural formula of

2,7-dibromo-benzo[2,1-b:3,4-b']dithiophene with a structural formula of and 5,8-di-(5-bromo-2-thienyl)-2,3-disubstituted-quinoxaline with a structural formula of are performed Stille coupling reaction for 24 to 72 hours with a mole ratio of m:p:q (m=p+q, m, p, q are positive real number) at a temperature of 60 to 132° C., in the first catalyst and the first organic solvent; then, reactant mixture containing the benzodithiophene organic semiconductive material with a structural formula of is obtained. Wherein, the first organic solvent is at least one of tetrahydrofuran (THF, same below), dimethoxyethane, benzene, chlorobenzene or toluene; and the first catalyst is organic palladium catalyst or a mixture of organic palladium and organic phosphine ligand, wherein the mole ratio of the organic palladium and the organic phosphine ligand is 1:1-20, and the organic palladium is selected from $Pd_2(dba)_3$, $Pd(PPh_3)_4$ or $Pd(PPh_3)_2Cl_2$, and the organic phosphine ligand is $P(o\text{-}Tol)_3$. The addition amount of the first catalyst is 0.01-30 mol % of the total substances.

The reaction equation is as follows:

wherein, x+y=2; 1≤x<2, 0<y≤1; 1<n≤100; $R_1$, $R_2$ are $C_1$-$C_{20}$ alkyl; $R_3$ is selected from $C_1$-$C_{20}$ alkyl; $R_4$, $R_5$ are hydrogen, phenyl, $C_1$-$C_{20}$ alkyl or phenyl substituted by $C_1$-$C_{20}$ alkoxy.

Another object of the present invention is to provide use of the organic semiconductive material in polymer solar cells, organic electroluminescent devices, organic field effect transistors, organic optical storages, organic nonlinear devices and organic laser devices, etc.

The present invention at least has the following advantages compared with the prior art:

1. Benzo[2,1-b:3,4-b']dithiophene unit of the organic semiconductive material of the present invention has a special molecular structure, where the two thiophene rings are on the same plane, thereby effectively extending conjugation of the organic semiconductive material, reducing energy gap, so that the carrier transferring between two main chain becomes easier, finally increasing carrier mobility;

2. The molecule structure of the organic semiconductive material of the present invention also contains a thiophene unit, and the unit is a five-membered ring structure in accordance with the Huckel's rule, having a moderate energy gap, relative wide spectral response, and better thermal stability and environmental stability; As a excellent receptor unit with a strong electron-withdrawing ability, quinoxaline unit has a high electron transport property, a high glass transition temperature, excellent electrochemical reduction properties, etc. And the quinoxaline unit can be modified easily, and electron donating group and electron acceptor group may be introduced to adjust its electron-withdrawing property according to a simple method.

3. Due to containing simultaneous benzo[2,1-b:3,4-b'] dithiophene structural unit, thiophene unit and quinoxaline unit, the organic semiconductive material of the present invention has the performance advantages of the units, expands sunlight absorption range of the organic the semiconductive material, and increases matching degree with solar radiation spectrum, thus effectively extends uses of the organic semiconductive material in polymer solar cells, organic electroluminescent devices, organic field effect transistors, organic optical memory devices or/and organic laser devices;

4. The preparation of the organic semiconductive material is by making limited reactants in a suitable reaction environment, and by controlling the temperature to react, thereby obtain a target product. Therefore, the preparation process is simple, easy to operate and control, and is suitable for industrial production.

DETAILED DESCRIPTION

The present invention provides a benzodithiophene organic semiconductive material with the following structure (P):

wherein, x+y=2; 1≤x<2, 0<y≤1; 1<n≤100; $R_1$, $R_2$ are $C_1$-$C_{20}$ alkyl; $R_3$ is selected from $C_1$-$C_{20}$ alkyl; $R_4$, $R_5$ are hydrogen, phenyl, $C_1$-$C_{20}$ alkyl or phenyl substituted by $C_1$-$C_{20}$ alkoxy.

The method for preparing the benzodithiophene organic semiconductive material is as follows:

Step S1: preparation of 5,8-di-(5-bromo-2-thienyl)-2,3-disubstituted-quinoxaline 3,6-dibromo-o-phenylenediamine and alkyl ethanedione are mixed and reacted to prepare 5,8-dibromo-2,3-disubstituted-quinoxaline, and the reaction formula is as follows:

Step S2: preparation of 5,8-di-(4-alkyl-2-thienyl)-2,3-disubstituted-quinoxaline In oxygen-free environment, the 5,8-dibromo-2,3-disubstituted-quinoxaline, 3-alkyl-2-thiophene borate and anhydrous sodium carbonate are added to the second organic solvent containing the second catalyst, and are reacted to obtain 5,8-di-(4-alkyl-2-thienyl)-2,3-disubstituted-quinoxaline; wherein the second catalyst is organic palladium or a mixture of organic palladium and organic phosphorus ligand; and the second organic solvent is at least one selected from tetrahydrofuran, ethyl ether, dichloromethane, chloroform or ethyl acetate; the reaction formula is as follows:

Step S3: preparation of 5,8-di-(5-bromo-4-alkyl-2-thienyl)-2,3-disubstituted-quinoxaline In oxygen free environment, N-bromosuccinimide and the 5,8-di-(4-alkyl-2-thienyl)-2,3-disubstituted-quinoxaline are added to a mixed solvent of sulfuric acid and trifluoroacetic acid, and they are reacted at a temperature of 10° C.-30° C. for 12 to 48 hours, to obtain 5,8-di-(5-bromo-4-alkyl-2-thienyl)-2,3-disubstituted-quinoxaline; and the reaction formula is as follows:

Step S4: preparation of 2,7-bis(trimethyltin)-benzo[2,1-b:3,4-b']dithiophene

At a temperature of −78° C. to −25° C., 4,5-dialkyl-benzo[2,1-b:3,4-b']dithiophene and butyl lithium (BuLi, hereafter the same) or n-butyl lithium (n-BuLi) or t-butyl lithium (t-BuLi) are added dropwise to the third organic solvent to mix, and then trimethyltin chloride ($Me_3SnCl$, hereafter the same) is added therein to prepare the 2,7-bis(trimethyltin)-benzo[2,1-b:3,4-b']dithiophene; wherein the third organic solvent is at least one selected from tetrahydrofuran, ethyl ether, dichloromethane, chloroform or ethyl acetate; the reaction formula is as follows:

Step S5: preparation of 2,7-dibromo-benzo[2,1-b:3,4-b']dithiophene

In oxygen free environment, N-bromosuccinimide (NBS, hereafter the same) and 4,5-dialkyl-benzo[2,1-b:3,4-b']dithiophene are added to a mixed solvent of sulfuric acid and trifluoroacetic acid, and they are reacted at a temperature of 10° C.-30° C. for 12 to 48 hours, to obtain the 4,4-dialkyl-2,6-dibromo-cyclopenta[2,1-b:3,4-b']dithiophene; and the reaction formula is as follows:

Step 6: preparation of a benzodithiophene organic semiconductive material In oxygen free environment, after 2,7-bis(trimethyltin)-benzo[2,1-b:3,4-b']dithiophene, 2,7-dibromo-benzo[2,1-b:3,4-b']dithiophene and 5,8-di-(5-bromo-2-thienyl)-2,3-disubstituted-quinoxaline with a mole ratio of m:p:q (m=p+q, m, p, q are real number) are performed Stille coupling reaction in catalyst and organic solvent at a temperature of 60-132° C. for 24 to 72 hours, a reactant mixture of the benzodithiophene organic semiconductive material containing a structural formula of is obtained.

The reaction formula is as follows:

wherein, x+y=2; $1 \leq x<2$, $0<y \leq 1$; $1<n \leq 100$; $R_1$, $R_2$ are same or different $C_1$-$C_{20}$ alkyl; $R_3$ is selected from $C_1$-$C_{20}$ alkyl; $R_4$, $R_5$ are same or different group selected from hydrogen, phenyl, $C_1$-$C_{20}$ alkyl or phenyl substituted by $C_1$-$C_{20}$ alkoxyl.

Step S7, the reactant mixture in step S6 is added dropwise to methanol, then is proceeded with settlement treatment, and then is filtered by suction, and is washed with methanol and is dried, to obtain organic semiconductive material containing impurities; then it is dissolved with toluene to give a toluene solution containing the organic semiconductive material;

Step S8, the toluene solution containing the organic semiconductive material of step S7 is added to an aqueous solution of sodium diethyldithiocarbamate, and the mixture is stirred and heated under 80-100° C. The mixture is purified by alumina column chromatography, and the organic semiconductive material is separated, and then eluted with chlorobenzene and subsequently chlorobenzene organic solvent is removed under reduced pressure, and finally the organic semiconductive material is extracted with acetone soxhlet extraction, to obtain a solid of the organic semiconductive material.

In the step 6 of the method for preparing the organic semiconductive material:

The first organic solvent is at least one selected from tetrahydrofuran (THF, hereafter the same), dimethoxyethane, benzene, chlorobenzene or toluene;

The first catalyst is an organic palladium catalyst or a mixture of organic palladium and organic phosphine ligand; wherein mole ratio of the mixture of the organic palladium and the organic phosphine ligand is 1:1 to 20, and the organic palladium is $Pd_2(dba)_3$, $Pd(PPh_3)_4$ or $Pd(PPh_3)_2Cl_2$, and the organic phosphine ligand is $P(o\text{-}Tol)_3$; and the addition amount of the first catalyst is 0.01-30 mol % of the total substances.

The oxygen free environment of the present invention is composed of nitrogen and/or inert gas.

Due to thiophene is with five-membered ring structure in accordance with the Huckel's rule, having a moderate energy gap, relative wide spectral response, better thermal stability and environmental stability, thiophene organic semiconductive material is a promising material, and its use in the field of photovoltaic has been studied extensively.

Benzo[2,1-b:3,4-b']dithiophene contains a rigid crystal structure—two thiophene rings in its structure unit are on the same plane. The structure may effectively extend conjugation of polymer, reducing its energy gap. And the coplanar structure makes the carrier transfer between two main chains easier, increasing carrier mobility accordingly. Based on the above properties, materials with a structure of benzo[2,1-b:3,4-b']dithiophene has been studied extensively in organic solar cells.

As an excellent receptor unit with a strong electron-withdrawing ability, quinoxaline unit has been widely used in optoelectronic materials. Compounds containing quinoxaline unit has a high electron transport property, a high glass transition temperature, excellent electrochemical reduction properties, etc. And the quinoxaline unit can be modified easily, and electron donating group and electron acceptor group may be introduced to adjust its electron-withdrawing property. Therefore, it has been used widely in organic optoelectronic materials.

However, currently there is no literature or patents reported the material containing the three units at the same time, which greatly limits its application range. Accordingly, the present invention has developed a benzodithiophene organic semiconductive material, and to expand their application range in the field of organic solar cells etc.

Preferred embodiments of the present invention will be described in further detail, with reference to the following drawings.

EXAMPLE 1

The embodiment discloses a benzodithiophene organic semiconductive material with the following structure:

wherein, x+y=2; 1≤x<2, 0<y≤1; 1<n≤100; $R_1$, $R_2$ are $C_1$-$C_{20}$ alkyl; $R_3$ is selected from $C_1$-$C_{20}$ alkyl; $R_4$, $R_5$ are $C_1$-$C_{20}$ alkyl.

A preparation process of the above mentioned material is as follows:

I: Compound 5,8-di-(5-bromo-4-substituted-2-thienyl)-2,3-dialkyl-quinoxaline is with the following structural formula:

Now the 5,8-di-(5-bromo-2-(4-dodecyl)-thienyl)-2,3-dioctyl-quinoxaline will be described as an example.

1) 5,8-dibromo-2,3-dioctyl-quinoxaline is with the following structural formula:

Now preparation of 5,8-dibromo-2,3-dioctyl-quinoxaline will be described as an example. The preparation process is described as follows:

At a temperature of 120° C., 3,6-dibromo-o-phenylenediamine (0.5 g, 1.85 mmol) was added into a compound of dioctyl ethanedione (0.28 g, 1 mmol) in acetic acid (30 mL) solution. The reaction mixture was refluxed overnight and poured into water, and neutralized with sodium bicarbonate to neutral. Then it was extracted with chloroform, washed with saturated brine, dried over with anhydrous sodium sulfate. The solvent was removed by rotary evaporation, and the crude product was by column chromatography to obtain a white solid, and then was recrystallized with chloroform/n-hexane to give the desired product. Yield 80%. MS (EI) m/z: 512 ($M^+$);

2) 5,8-di-(4-dodecyl-2-thienyl)-2,3-dioctyl-quinoxaline

Under a nitrogen atmosphere, a mixture of tetrahydrofuran aqueous solution (THF 80 mL; $H_2O$, 20 mL) containing 5,8-dibromo-2,3-dioctyl quinoxaline (0.85 g, 1.67 mmol), 3-dodecyl-2-thiophene borate (1.5 g, 4.0 mmol), anhydrous sodium carbonate (5.3 g, 50 mmol), $Pd(PPh_3)_4$ (0.1 g, 0.08 mmol) was heated to reflux, then stirred overnight. The reaction solution was poured into water, filtered by suction, washed with water, and the resulting crude product was purified by column chromatograph to obtain product, with a yield 65%. MS (MALDI) m/z: 855 (+);

3) 5,8-di-(5-bromo-4-dodecyl-2-thienyl)-2,3-dioctyl-quinoxaline

Under a nitrogen atmosphere, NBS (0.54, 3.0 mmol) was added to tetrahydrofuran solution (THF 50 mL) containing 5,8-di(2-thienyl)-2,3-dioctyl-quinoxaline (1.2 g, 1.4 mmol), and stirred at room temperature overnight. The reaction solution was rotary to dry to obtain the crude product, and the crude product is purified by column chromatography to obtain the product, with a yield 77%. MS (MALDI) m/z: 1013 (M+);

II: Compounds 2,7-dibromo-4,5-dialkyl-substituted benzo[2,1-b:3,4-b']dithiophene and 2,7-bis trimethyltin-4,5-dialkyl substituted benzo[2,1-b:3,4-b']dithiophene are with the following structural formula:

Corresponding product is prepared according to a method disclosed by *Macromolecules* 2008, 41, 5688. 2,7-bis(trimethyltin)-4,5-dioctyl benzoe[2,1-b:3,4-b']dithiophene will be described as an example.

At a temperature of −78° C., t-BuLi (5.3 mL, 1.4 mol/L, 7.5 mmol) was added dropwise to a tetrahydrofuran solution (100 mL) containing 4,5-dioctyl benzo[2,1-b:3,4-b']dithiophene (1.03 g, 2.5). The mixture was slowly recovered to room temperature, and stirred for 0.5 h, and then cooled to −78° C. Trimethyltin chloride (7.5 mmol, 7.5 mL) was added dropwise to the solution. The solution was slowly recovered to room temperature and stirred overnight. The reaction solution was quenched with water, rotary evaporated to remove tetrahydrofuran, extracted with chloroform/water, washed with water, dried with anhydrous sodium sulfate. Organic phase was removed to give a brown solid with a yield 54%. MS (MALDI) m/z: 617 (M+).

The following is a preparation process of the benzodithiophene organic semiconductive materials ($P_1$, $P_2$, $P_3$, $P_4$, $P_5$, $P_6$, $P_7$) of Embodiment 1, wherein, $R_4$, $R_5$ are $C_1$-$C_{20}$ alkyl.

III. Benzodithiophene organic semiconductor $P_1$ n = 47
x = 1, y = 1

Under a nitrogen atmosphere, chlorobenzene (25 mL) solution containing compounds 5,8-di-(5-bromo-2-thienyl)-2,3-dioctyl-quinoxaline (0.34 g, 0.5 mmol), 2,7-bis(trimethyltin)-4-methyl-5-n-eicosyl benzo[2,1-b:3,4-b']dithiophene (0.41 g, 0.5 mmol) was purged with nitrogen, and bubbled for 0.5 hour to remove residual oxygen. Then $Pd_2(dba)_3$ (0.014 g, 0.015 mmol) and $P(o\text{-Tol})_3$ (0.0083 g, 0.027 mmol) were added. Continue to purse into the nitrogen gas, and bubble for 1 hour to remove residual oxygen and then heat to 100° C. for 45 hours, finally a reactant mixture of the benzodithiophene organic semiconductor $P_1$ was obtained.

The mixture was added to methanol to precipitate, filtered by suction, washed with methanol and dried; then dissolved with chlorobenzene, and added to an aqueous solution of sodium diethyldithiocarbamate. The mixture was then heated to 80° C. and stirred overnight. Organic phase was purified by alumina-column chromatography, and eluted with chloroform. Organic solvent was removed under reduced pressure, and the remainder was precipitated with methanol, and filtered by suction, the resulting solid was extracted with acetone soxhlet extraction for three days; then precipitated with methanol, filtered by suction, and the resulting solid of the benzodithiophene organic semiconductor $P_1$ obtained overnight was pumped by vacuum pump, with a yield 62%. Molecular weight (GPC, THF, R. I): $M_n=47500$, $M_w/M_n=2.3$).

IV. Benzodithiophene organic semiconductor $P_2$

P2
n = 25
x = 1, y = 1

Under a nitrogen atmosphere, a chlorobenzene (25 mL) solution containing compounds 5,8-di-(5-bromo-4-n-dodecyl-2-thienyl)-quinoxaline (0.39 g, 0.5 mmol) and 2,7-bis(trimethyltin)-4,5-dioctyl benzo[2,1-b:3,4-b']dithiophene (0.37 g, 0.5 mmol) was purged with the nitrogen gas, and bubbled for 0.5 h to remove residual oxygen. Then $Pd_2(dba)_3$ (0.014 g, 0.015 mmol) and $P(o\text{-Tol})_3$ (0.0083 g, 0.027 mmol) were added. Continue to purge with the nitrogen gas, and to bubble for 1 hour to remove residual oxygen and then heat to 132° C. and react for 48 hours, finally a reactant mixture of the benzodithiophene organic semiconductor $P_2$ was obtained.

The mixture was added to methanol to precipitate, filtered by suction, washed with methanol and dried; then dissolved with chlorobenzene, and added to an aqueous solution of sodium diethyldithiocarbamate. The mixture was then heated to 80° C. and stirred overnight. Organic phase was purified by alumina-column chromatography, and eluted with chloroform. Organic solvent was removed under reduced pressure, and the remainder was precipitated with methanol, and filtered by suction; the resulting solid was extracted with acetone soxhlet extraction for three days, precipitated with methanol, and filtered by suction, then the resulting solid of the benzodithiophene organic semiconductor $P_2$ obtained overnight was pumped by vacuum pump, with a yield 51%. Molecular weight (GPC, THF, R. I): $M_n=26500$, $M_w/M_n=1.9$).

V. Benzodithiophene organic semiconductor $P_3$

P3
n = 50
x = 1, y = 1

Under a nitrogen atmosphere, a chlorobenzene (25 mL) solution containing compounds 5,8-di-(5-bromo-4-n-eicosyl-2-thienyl)-2-methyl-3-n-eicosyl-quinoxaline (0.65 g, 0.5 mmol) and 2,7-bis(trimethyltin)-4,5-dioctyl benzoe[2,1-b:3,4-b']dithiophene (0.37 g, 0.5 mmol) was purged with the nitrogen gas, and bubbled for 0.5 hour to remove residual oxygen. Then $Pd_2(dba)_3$ (0.014 g, 0.015 mmol) and $P(o\text{-Tol})_3$ (0.0083 g, 0.027 mmol) were added. Continue to purge with the nitrogen gas, and bubble for 1 hour to remove residual oxygen and then heat to 80° C. and react for 55 hours, finally a reactant mixture of the benzodithiophene organic semiconductor $P_3$ was obtained.

The mixture was added to methanol to precipitate, filtered by suction, washed with methanol and dried; then dissolved with chlorobenzene, and added to an aqueous solution of sodium diethyldithiocarbamate. The mixture was then heated to 90° C. and stirred overnight. Organic phase was purified by alumina-column chromatography, and eluted with chloroform. Organic solvent was removed under reduced pressure, and the remainder was precipitated with methanol, and filtered by suction, the resulting solid was extracted with acetone soxhlet extraction for three days; and then precipitated with methanol, filtered by suction, and the resulting solid of the benzodithiophene organic semiconductor $P_3$ obtained overnight was pumped by vacuum pump, with a yield 60%. Molecular weight (GPC, THF, R. I): $M_n=78300$, $M_w/M_n=2.1$).

VI. Benzodithiophene organic semiconductor P₄

P4
n = 7
x = 1, y = 1

P5
n = 66
x = 1.5, y = 0.5

Under an argon atmosphere, a chlorobenzene (25 mL) solution containing compounds 5,8-di-(5-bromo-4-methyl-2-thienyl)-2,3-dioctyl-quinoxaline (0.35 g, 0.5 mmol) and 2,7-bis(trimethyltin)-4,5-dioctyl benzoe[2,1-b:3,4-b'] dithiophene (0.37 g, 0.5 mmol) was purged with the argon gas, and bubbled for 0.5 hour to remove residual oxygen. Then $Pd_2(dba)_3$ (0.014 g, 0.015 mmol) and P(o-Tol)₃ (0.0083 g, 0.027 mmol) were added. Continue to purge with the argon gas, and bubble for 1 hour to remove residual oxygen and then heat to 60° C. and react for 69 hours, finally a reactant mixture of the benzodithiophene organic semiconductor P₄ was obtained.

The mixture was added to methanol to precipitate, filtered by suction, washed with methanol and dried; then dissolved with chlorobenzene, and added to an aqueous solution of sodium diethyldithiocarbamate. The mixture was then heated to 100° C. and stirred overnight. Organic phase was purified by alumina-column chromatography, and eluted with chloroform. Organic solvent was removed under reduced pressure, and the remainder was precipitated with methanol, and filtered by suction, the resulting solid was extracted with acetone soxhlet extraction for three days; and precipitated with methanol, filtered by suction, and the resulting solid of the benzodithiophene organic semiconductor P₄ obtained overnight was pumped by vacuum pump, with a yield 48%.

Molecular weight (GPC, THF, R. I): $M_n$=6900, $M_w/M_n$=2.3).

VII. Benzodithiophene organic semiconductor P₅

Under a nitrogen and argon atmosphere, a chlorobenzene (25 mL) solution containing compounds 5,8-di-(5-bromo-4-n-dodecyl-2-thienyl)-2,3-dioctyl-quinoxaline (0.25 g, 0.25 mmol), 2,7-dibromo-4,5-dioctyl benzo[2,1-b:3,4-b'] dithiophene (0.14 g, 0.25 mmol) and 2,7-bis(trimethyltin)-4,5-dioctyl benzoe[2,1-b:3,4-b']dithiophene (0.37 g, 0.5 mmol) was purged with the nitrogen and argon mixed gas, and bubbled for 0.5 hour to remove residual oxygen. Then $Pd_2(dba)_3$ (0.014 g, 0.015 mmol) and P(o-Tol)₃ (0.0083 g, 0.027 mmol) were added. Continue to purge with the nitrogen and argon mixed gas, and bubble for 1 hour to remove residual oxygen and then heat to 80° C. and react for 40 hours, finally a reactant mixture of the benzodithiophene organic semiconductor P₅ was obtained.

The mixture was added to methanol to precipitate, filtered by suction, washed with methanol and dried; then dissolved with chlorobenzene, and added to an aqueous solution of sodium diethyldithiocarbamate. The mixture was then heated to 95° C. and stirred overnight. The organic phase was purified by alumina-column chromatography, and eluted with chloroform. The organic solvent was removed under reduced pressure, and the remainder was precipitated with methanol, and filtered by suction, the resulting solid was extracted with acetone soxhlet extraction for three days; and precipitated with methanol, filtered by suction, and the resulting solid of the benzodithiophene organic semiconductor P₅ obtained overnight was pumped by vacuum pump, with a yield 61%.

Molecular weight (GPC, THF, R. I): $M_n$=68900, $M_w/M_n$=1.9).

VIII. Benzodithiophene organic semiconductor P₆ n = 100
x = 1.9, y = 0.1

Under a nitrogen atmosphere, a chlorobenzene (25 mL) solution containing compounds 5,8-di-(5-bromo-4-n-dodecyl-2-thienyl)-2,3-dioctyl-quinoxaline (0.13 g, 0.05 mmol), 2,7-dibromo-4,5-dioctyl benzo[2,1-b:3,4-b']dithiophene (0.26 g, 0.45 mmol) and 2,7-bis trimethyltin-4,5-dioctyl benzoe[2,1-b:3,4-b']dithiophene (0.37 g, 0.5 mmol) was purged with the nitrogen gas, and bubbled for 0.5 hour to remove residual oxygen. Then $Pd_2(dba)_3$ (0.014 g, 0.015 mmol) and $P(o\text{-Tol})_3$ (0.0083 g, 0.027 mmol) were added. Continue to purge with the nitrogen gas, and bubble for 1 hour to remove residual oxygen and then heat to 70° C. and react for 65 hours, finally a reactant mixture of the benzodithiophene organic semiconductor $P_6$ was obtained.

The mixture was added to methanol to precipitate, filtered by suction, washed with methanol and dried; then dissolved with chlorobenzene, and added to an aqueous solution of sodium diethyldithiocarbamate. The mixture was then heated to 80° C. and stirred overnight. The organic phase was purified by alumina-column chromatography, and eluted with chloroform. The organic solvent was removed under reduced pressure, and the remainder was precipitated with methanol, and filtered by suction, the resulting solid was extracted with acetone soxhlet extraction for three days; and precipitated with methanol, filtered by suction, and the resulting solid of the benzodithiophene organic semiconductor $P_6$ obtained overnight was pumped by vacuum pump. Yield 41%. Molecular weight (GPC, THF, R. I): $M_n=87500$, $M_w/M_n=1.9$).

VX. Benzodithiophene organic semiconductor $P_7$ n = 63
x = 1, y = 1;

Under a nitrogen atmosphere, a chlorobenzene (25 mL) solution containing compounds 5,8-bis-(5-bromo-4-n-dodecyl-2-thienyl)-quinoxaline (0.51 g, 0.5 mmol) and 2,7-bis (trimethyltin)-4,5-dioctyl benzoe[2,1-b:3,4-b']dithiophene (0.37 g, 0.5 mmol) was purged with the nitrogen gas, and bubbled for 0.5 hour to remove residual oxygen. Then $Pd_2(dba)_3$ (0.014 g, 0.015 mmol) and $P(o\text{-Tol})_3$ (0.0083 g, 0.027 mmol) were added. Continue to purge with the nitrogen gas, and bubble for 1 h to remove residual oxygen and then heat to 110° C. and react for 40 hours, finally a reactant mixture of the benzodithiophene organic semiconductor $P_7$ was obtained.

The mixture was added to methanol to precipitate, filtered by suction, washed with methanol and dried; then dissolved with chlorobenzene, and added to an aqueous solution of sodium diethyldithiocarbamate. The mixture was then heated to 80° C. and stirred overnight. The organic phase was purified by alumina-column chromatography, and eluted with chloroform. The organic solvent was removed under reduced pressure, and the remainder was precipitated with methanol, and filtered by suction, the resulting solid was extracted with acetone soxhlet extraction for three days; and precipitated with methanol, filtered by suction, and the resulting solid of the benzodithiophene organic semiconductor $P_7$ obtained overnight was pumped by vacuum pump. Yield 46%. Molecular weight (GPC, THF, R. I): $M_n=79500$, $M_w/M_n=2.1$).

EXAMPLE 2

The present embodiment discloses a benzodithiophene organic semiconductive material with the following structural formula:

wherein, x+y=2; 1≤x<2, 0<y<1; 1<n≤100; $R_1$, $R_2$ are $C_1$-$C_{20}$ alkyl; $R_3$ is selected from $C_1$-$C_{20}$ alkyl; $R_4$, $R_5$ are phenyl substituted by $C_1$-$C_{20}$ alkyl.

The preparation process of the organic semiconductive material is as follows:

I. 5,8-di-(5-bromo-2-thienyl)-2,3-diphenyl-quinoxaline

The preparation of 5,8-di-(5-bromo-4-n-eicosyl-2-thienyl)-2,3-diphenyl-quinoxaline is described as a example as follows:

Under a nitrogen atmosphere, NBS (0.6 g, 3.3 mmol) was added to tetrahydrofuran solution (THF 50 mL) containing 5,8-di-(4-n-dodecyl-2-thienyl)-2,3-dioctyl-quinoxaline (1.2 g, 1.53 mmol), and stirred at room temperature overnight. The reaction solution was rotary to dry to obtain crude product, and the crude product was by column chromatography to obtain the product 1.05 g, with a yield 73%. MS (MALDI) m/z: 941 (M⁺);

Wherein, the preparation of 2,7-bis trimethyltin-benzo[2,1-b:3,4-b']dithiophene and the preparation of 2,7-dibromo-benzo[2,1-b:3,4-b']dithiophene are reference with embodiment 1.

The following is a preparation process of benzodithiophene organic semiconductive materials ($P_3$, $P_9$, $P_{10}$) of embodiment 2, wherein, $R_1$, $R_2$, $R_3$ are $C_1$-$C_{20}$ alkyl, and $R_4$, $R_5$ are phenyl substituted by $C_1$-$C_{20}$ alkyl.

II. Benzodithiophene Organic Semiconductor $P_8$ n = 45
x = 1, y = 1;

Under a nitrogen atmosphere, a toluene (25 mL) solution containing compounds 5,8-di-(5-bromo-4-n-dodecyl-2-thienyl)-2,3-diphenyl-quinoxaline (0.47 g, 0.5 mmol) and 2,7-bis trimethyltin-4,5-dioctyl benzoe[2,1-b:3,4-b']dithiophene (0.37 g, 0.5 mmol) was purged with the nitrogen gas, and bubbled for 0.5 hour to remove residual oxygen. Then $Pd_2(dba)_3$ (0.014 g, 0.015 mmol) and $P(o-Tol)_3$ (0.0083 g, 0.027 mmol) were added. Continue to purge with the nitrogen gas, and bubble for 1 hour to remove residual oxygen and then heat to 100° C. and react for 72 hours, finally a reactant mixture of the benzodithiophene organic semiconductor $P_8$ was obtained.

The mixture was added to methanol to precipitate, filtered by suction, washed with methanol and dried; then is dissolved with chlorobenzene, and added to an aqueous solution of sodium diethyldithiocarbamate. The mixture was then heated to 80° C. and stirred overnight. The organic phase was purified by alumina-column chromatography, and eluted with chloroform. The organic solvent was removed under reduced pressure, and the remainder was precipitated with methanol, and filtered by suction, the resulting solid was extracted with acetone soxhlet extraction for three days; and precipitated with methanol, filtered by suction, and the resulting solid of the benzodithiophene organic semiconductor $P_8$ obtained overnight was pumped by vacuum pump. Yield 58%. Molecular weight (GPC, THF, R. I): $M_n$=54500, $M_w/M_n$=2.1).

III. Benzodithiophene Organic Semiconductor $P_9$

P9
n = 33
x = 1, y = 1;

Under a nitrogen atmosphere, a toluene (25 mL) solution containing compounds 5,8-di-(5-bromo-4-n-dodecyl-2-thienyl)-2-(4-methylphenyl)-3-(4-n-eicosyl phenyl)-quinoxaline (0.62 g, 0.5 mmol) and 2,7-bis trimethyltin-4,5-dioctyl benzoe[2,1-b:3,4-b']dithiophene (0.37 g, 0.5 mmol) was purged with the nitrogen gas, and bubbled for 0.5 hour to remove residual oxygen. Then $Pd_2(dba)_3$ (0.014 g, 0.015 mmol) and $P(o-Tol)_3$ (0.0083 g, 0.027 mmol) were added. Continue to purge with the nitrogen gas, and bubble for 1 hour to remove residual oxygen and then heat to 80° C. and react for 68 hours, finally a reactant mixture of the benzodithiophene organic semiconductor $P_9$ was obtained.

The mixture was added to methanol to precipitate, filtered by suction, washed with methanol and dried; then dissolved with chlorobenzene, and added to an aqueous solution of sodium diethyldithiocarbamate. The mixture was then heated to 80° C. and stirred overnight. The organic phase was purified by alumina-column chromatography, and eluted with chloroform. The organic solvent was removed under reduced pressure, and the remainder was precipitated with methanol, and filtered by suction, the resulting solid was extracted with acetone soxhlet extraction for three days; and precipitated with methanol, filtered by suction, and the resulting solid of the benzodithiophene organic semiconductor $P_9$ obtained overnight was pumped by vacuum pump. Yield 37%. Molecular weight (GPC, THF, R. I): $M_n$=48500, $M_w/M_n$=1.7).

IV. Benzodithiophene Organic Semiconductor $P_{10}$

P10
n = 22
x = 1, y = 1;

Under a nitrogen atmosphere, a toluene (25 mL) solution containing compounds 5,8-di-(5-bromo-4-n-dodecyl-2-thienyl)-2,3-di(4-octylphenyl)-quinoxaline (0.58 g, 0.5 mmol) and 2,7-bis trimethyltin-4,5-dioctyl benzoe[2,1-b:3,4-b']dithiophene (0.37 g, 0.5 mmol) was purged with the nitrogen gas, and bubbled for 0.5 hour to remove residual oxygen. Then $Pd_2(dba)_3$ (0.014 g, 0.015 mmol) and $P(o-Tol)_3$ (0.0083 g, 0.027 mmol) were added. Continue to purge with the nitrogen gas, and bubble for 1 hour to remove residual oxygen and then heat to 90° C. and react for 70 hours, finally a reactant mixture of the benzodithiophene organic semiconductor $P_{10}$ was obtained.

The mixture was added to methanol to precipitate, filtered by suction, washed with methanol and dried; then dissolved with chlorobenzene, and added to an aqueous solution of sodium diethyldithiocarbamate. The mixture was then heated to 80° C. and stirred overnight. The organic phase was purified by alumina-column chromatography, and eluted with chloroform. The organic solvent was removed under reduced pressure, and the remainder was precipitated with methanol, and filtered by suction, the resulting solid was extracted with acetone soxhlet extraction for three days; and precipitated with methanol, filtered by suction, and the resulting solid of the benzodithiophene organic semiconductor $P_{10}$ obtained overnight was pumped by vacuum pump. Yield 58%. Molecular weight (GPC, THF, R. I): $M_n$=31500, $M_w/M_n$=1.9).

The present invention also provides uses of a benzodithiophene organic semiconductive material with a structural formula (wherein, x+y=2; 1≤x<2, 0<y≤1; 1<n≤100; $R_1$, $R_2$ are the same or different $C_1$-$C_{20}$ alkyl; $R_3$ is selected from $C_1$-$C_{20}$ alkyl; $R_4$, $R_5$ are the same or different hydrogen, phenyl, $C_1$ to $C_{20}$ alkyl or phenyl substituted by $C_1$-$C_{20}$ alkoxy) in the field of polymer solar cells, organic electroluminescent devices, organic field effect transistors, organic optical storage, organic non-linear devices and organic laser devices, etc.

The following embodiment is described the uses of the benzodithiophene organic semiconductive material in the field of organic solar cells, organic field effect transistors and organic electroluminescent devices.

EXAMPLE 3

Figure 1:
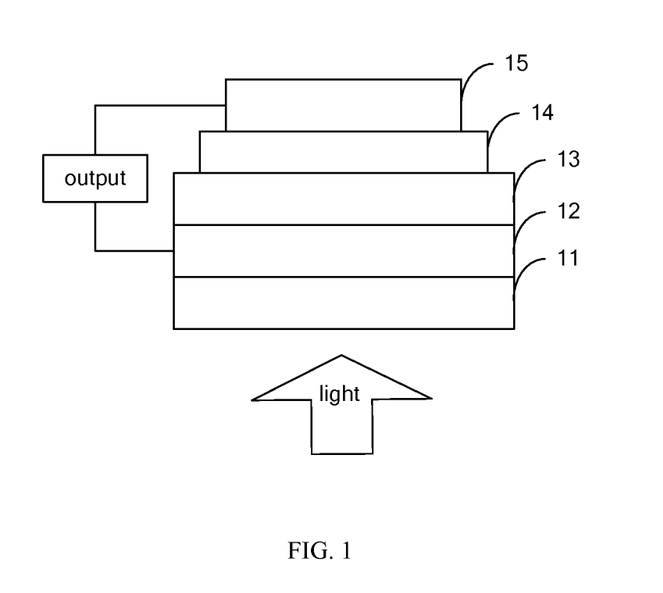
FIG. 1 illustrates a structural schematic diagram of an organic solar cell device with an organic semiconductive material according to the present invention as an active layer.

A structure of a polymer solar cell device is illustrated in FIG. 1. Wherein, in the present embodiment a substrate was adopted ITO glass, and glass was used as a substrate, and ITO was as a conductive layer.

The structure of the polymer solar cell device was: glass 11/ITO layer 12/PEDOT: PSS layer 13/active layer 14/Al layer 15; wherein material of the active layer was a benzodithiophene organic semiconductive material of the present invention; ITO was indium tin oxide with square resistance of 10-20 Ohms per square, and PEDOT was poly(3,4-ethylenedioxy-thiophene), and PSS was poly(styrene sulfonic acid); and preferably ITO was with a square resistance of 10 Ohms and with a thickness of about 50-300 nm.

The preparation of the polymer solar cell device is as follows:

A layer of indium tin oxide (ITO) 12 with square resistance of 10-20 Ohms per square was deposited on one surface of glass substrate 11, to form the conductive layer as an anode, with a thickness of about 50-300 nm;

After ITO glass was cleaned by ultrasonic wave and treated with oxygen plasma, and a layer of PEDOT:PSS layer 13 was coated on the ITO surface as a modified function, with a thickness of about 20-300 nm;

A layer of active layer 14 was coated on the poly(3,4-ethylenedioxy thiophene): PSS (poly(styrene sulfonic acid)) layer 13 by spin-coating, with a thickness of about 50-300 nm; and the material of the active layer was the benzodithiophene organic semiconductive material of the present invention;

Metallic aluminum was deposited on the surface of the active layer by vacuum evaporation method, to form the metallic aluminum layer 15 as a cathode, obtaining the organic solar cell device;

After the polymer solar cell device was encapsulated with epoxy resin, place it under 120° C. in sealed condition and anneal for 2 hours, and then cool down to room temperature. Because the device after annealing, the chemical structure of the material was more regular and orderly, it improved the transmission speed and efficiency of the carrier, thereby improved the photoelectric conversion efficiency of the device.

Preferably, the thickness of ITO, PEDOT: PSS, the active layer, the Al layer are respectively 110 nm, 60 nm, 110 nm and 100 nm.

EXAMPLE 4

Figure 2:
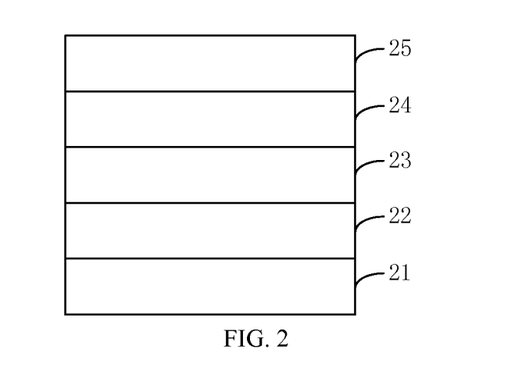
FIG. 2 illustrates a structural schematic diagram of an organic electroluminescent device with an organic semiconductive material according to the present invention as a luminous layer.

A structure of an organic electroluminescent device is illustrated in FIG. 2. In the present embodiment a substrate was adopted ITO glass, and glass was used as a substrate, and ITO was as a conductive layer.

The structure of the organic electroluminescent device was: glass 21/ITO layer 22/luminous layer 23/LiF buffer layer 24/Al layer 25; wherein, the material of the luminous layer is a benzodithiophene organic semiconductive material of the present invention.

The preparation of the organic electroluminescent device is as follows:

A layer of indium tin oxide (ITO) layer 22 with a square resistance of 10-20 Ohms was deposited on one surface of glass substrate 21, to form the a conductive layer as an anode, with a thickness of about 50-300 nm; and ITO was preferably with a square resistance of 10 Ohms;

On surface of the ITO, the luminous layer 23 was prepared with a material of a benzodithiophene organic semiconductive material of the present invention by spin-coating, with a thickness of about 50-300 nm;

LiF was deposited on the luminous layer by vacuum evaporation method, as the buffer layer 24, with a thickness of about 0.3-2 nm;

Metallic aluminum was deposited on the luminous layer by vacuum evaporation method, to form the metallic aluminum layer 25 as a cathode, obtaining the organic electroluminescent device.

EXAMPLE 5

Figure 3:
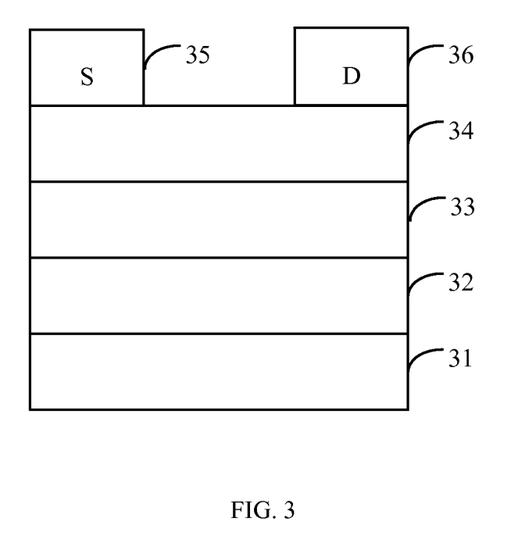
FIG. 3 illustrates a structural schematic diagram of an organic field effect transistor with an organic semiconductive material according to the present invention as an organic semiconductor layer.

A structure of an organic field effect transistor is illustrated in FIG. 3. In the present embodiment a substrate was adopted doped silicon (Si).

The structure of the organic field effect transistor was: Si 31/$SiO_2$ insulation layer with a thickness of 450 nm 32/octadecyltrichlorosilane (OTS) layer for modifying $SiO_2$ 33/organic semiconductor layer 34/a source electrode (S) 35 and a drain electrode (D) 36 with gold as a material; wherein, the material of the organic semiconductor layer was a benzodithiophene organic semiconductive material of the present invention; wherein, the material of the source electrode (S) and the drain electrode (D) may also be copper.

The preparation process of the organic field effect transistor is:

First, on one surface of the doped silicon 31 which was cleaned, a layer of SiO$_2$ insulation layer 32 was coated; secondly, on the SiO$_2$ insulation layer, a layer of octadecyl trichlorosilane layer 33 was coated as a function of modification with a thickness of 10-200 nm; Then, on the octadecyl trichlorosilane layer, an organic semiconductor layer 34 with a material of benzodithiophene organic semiconductor of the present invention was coated by spin-coating with a thickness of 30-300 nm; Finally, the source electrode (S) 35 and the drain electrode (D) 36 with gold as material were arranged interval in the organic semiconductor layer, to obtain the organic field effect transistor.

Although the invention has been described in language specific to structural features and/or methodological acts, it is to be understood that the invention defined in the appended claims is not necessarily limited to the specific features or acts described. Rather, the specific features and acts are disclosed as sample forms of implementing the claimed invention.

What is claimed is:

1. A benzodithiophene organic semiconductive material with the following structural formula(P):

(P)

wherein, x+y=2; 1≤x<2, 0<y≤1; 1<n≤100; $R_1$, $R_2$ are $C_1$-$C_{20}$ alkyl; $R_3$ is selected from $C_1$-$C_{20}$ alkyl; $R_4$, $R_5$ are hydrogen, phenyl, $C_1$-$C_{20}$ alkyl or phenyl substituted by $C_1$-$C_{20}$ alkoxy.

2. A method for preparing a benzodithiophene organic semiconductive material, wherein the method comprises the following steps:

in oxygen free environment, with the presence of the first catalyst and the first organic solvent, conducting Stille coupling reaction by using 2,7-bis(trimethyltin)-benzo[2,1-b :3,4-b'] dithiophene with a structural formula of

2,7-dibromo-benzo[2,1-b:3,4-b'] dithiophene with a structural formula of and 5,8-di-(5-bromo-2-thienyl)-2,3-disubstituted-quinoxaline with a structural formula of to obtain a reactant mixture containing the benzodithiophene organic semiconductive material with a structural formula of wherein, x+y=2; 1≤x<2, 0<y≤1; 1<n ≤100; $R_1$, $R_2$ are $C_1$-$C_{20}$ alkyl; $R_3$ is selected from $C_1$-$C_{20}$ alkyl; $R_4$, $R_5$ are hydrogen, phenyl, $C_1$-$C_{20}$ alkyl or phenyl substituted by $C_1$-$C_{20}$ alkoxy.

3. The method according to claim 2, wherein the 5,8-di-(5-bromo-2-thienyl)-2,3-disubstituted-quinoxaline is prepared by the following steps:

mixing and reacting 3,6-dibromo-o-phenylenediamine with alkyl ethoxylated dione to prepare 5,8-dibromo-2,3-disubstituted-quinoxaline;

in oxygen-free environment, adding the 5,8-dibromo-2,3-disubstituted-quinoxaline, 3-alkyl-2-thiophene borate and anhydrous sodium carbonate into the second organic solvent containing the second catalyst, to obtain 5,8-di-(4-alkyl-2-thienyl)-2,3-disubstituted-quinoxaline by reaction; wherein the second catalyst is organic palladium or a mixture of organic palladium and organic phosphorus ligand; and the second organic solvent is at least one selected from tetrahydrofuran, ethyl ether, dichloromethane, chloroform or ethyl acetate;

in oxygen free environment, adding N-bromosuccinimide and the 5,8-di-(4-alkyl-2- thienyl)-2,3-disubstituted-quinoxaline into a mixed solvent of sulfuric acid and trifluoroacetic acid, and reacting them at a temperature of 10° C.-30° C. for 12 to 48 hours, to obtain 5,8-di-(5-bromo-4-alkyl-2-thienyl)-2,3-disubstituted- quinoxaline.

4. The method according to claim 2, wherein, the 2,7-bis(trimethyltin)- benzo[2,1-b:3,4-b'] dithiophene is prepared by the following step:

at a temperature of −78° C. to −25° C., adding 4,5-dialkyl-benzo[2,1-b:3,4-b'] dithiophene and butyl lithium into a third organic solvent by dropwise, mixing them, and then adding trimethyltin chloride thereinto, to prepare the 2,7-bis-trimethyltin -benzo[2,1-b:3,4-b'] dithiophene; wherein the third organic solvent is at least one selected from tetrahydrofuran, ethyl ether, dichloromethane, chloroform or ethyl acetate.

5. The method according to claim 2, wherein the 2,7-dibromo-benzo [2,1-b:3,4-b'] dithiophene is prepared by the following step:

in oxygen free environment, adding N-bromosuccinimide and 4,5-dialkyl-benzo [2,1-b :3,4-b'] dithiophene into a mixed solvent of sulfuric acid and trifluoroacetic acid, and reacting them at a temperature of 10° C.-30° C. for 12 to 48 hours, to obtain 4,4-dialkyl-2,6-dibromo-cyclopenta[2,1-b:3,4-b'] dithiophene.

6. The method according to claim 2, wherein the addition amount of the first catalyst is 0.01-30 mol % of the total substances; and the first catalyst is organic palladium or a mixture of organic palladium and organic phosphine ligand;

the organic palladium is at least one selected from $Pd_2(dba)_3$, $Pd(PPh_3)_4$ or $Pd(PPh_3)_2Cl_2$;

the organic phosphine ligand is $P(o-Tol)_3$;

wherein, in the mixture of organic palladium and organic phosphine ligand, the mole ratio of the organic palladium and the organic phsophine ligand is 1: 1-20.

7. The method according to claim 2, wherein the first organic solvent is at least one selected from tetrahydrofuran, ethylene glycol dimethyl ether, benzene, chlorobenzene or toluene.

8. The method according to claim 2, wherein in the Stille coupling reaction, the mole ratio of the 2,7-bis(trimethyltin)-benzo[2,1-b:3,4-b'] dithiophene, 2,7-dibromo-benzo[2,1-b:3,4-b'] dithiophene and 5,8-di-(5-bromo-2-thienyl)-2,3-disubstituted-quinoxaline is m:p:q, and m=p+q, m, p, q are positive real number; reaction temperature of the Stille coupling reaction is 60-132° C., and reaction time is 24-72 hours.

9. The method according to claim 2, wherein after the Stille coupling reaction, it further comprises a step of purifying the reactant mixture:

adding the reactant mixture into methanol by dropwise, proceeding settlement treatment, then conducting suction filtration, washing them with methanol and drying, to obtain a colloid containing the organic semiconductive material; then dissolving the colloid with toluene to obtain a toluene solution of the organic semiconductive material;

adding the toluene solution of the semiconductive material into an aqueous solution of sodium diethyldithiocarbamate, heating and stirring the mixture at 80-100° C., and purifying the mixture by alumina column chromatography to separate the organic semiconductive material, and then, eluting the material with chlorobenzene, subsequently removing chlorobenzene organic solvent under reduced pressure, and finally extracting the organic semiconductive material with acetone soxhlet extraction to obtain a solid of the organic semiconductive material.

10. The benzodithiophene organic semiconductive material according to claim 1 for use as a component part of polymer solar cells, organic electroluminescent devices, organic field effect transistors, organic optical storage, organic non-linear devices and organic laser devices.

\* \* \* \* \*